(12) United States Patent
Greggs

(10) Patent No.: US 7,232,311 B1
(45) Date of Patent: Jun. 19, 2007

(54) BUR FOR PREPARING METAL SUBSTRATES

(76) Inventor: Thomas S. Greggs, 50 Village Walk, Wilton, CT (US) 06897

( * ) Notice: Subject to any disclaimer, the term of this patent is extended or adjusted under 35 U.S.C. 154(b) by 366 days.

(21) Appl. No.: 10/414,924

(22) Filed: Apr. 16, 2003

Related U.S. Application Data

(60) Provisional application No. 60/374,094, filed on Apr. 19, 2002.

(51) Int. Cl.
*A61C 3/02* (2006.01)

(52) U.S. Cl. ..................................... 433/165

(58) Field of Classification Search ................ 433/165, 433/166; 407/59, 61, 57; 408/213
See application file for complete search history.

(56) References Cited

U.S. PATENT DOCUMENTS

| | | | | |
|---|---|---|---|---|
| 418,108 A | * | 12/1889 | Browne | 433/165 |
| 843,273 A | * | 2/1907 | Homann | 433/165 |
| 1,358,432 A | * | 11/1920 | Fink | 433/165 |
| 1,813,741 A | * | 7/1931 | Harper | 433/165 |
| 2,606,366 A | * | 8/1952 | Stevens | 433/166 |
| 4,174,915 A | * | 11/1979 | Peetz et al. | 407/59 |
| 4,285,618 A | * | 8/1981 | Shanley, Jr. | 407/54 |
| 5,193,944 A | * | 3/1993 | Nishimura | 407/53 |
| 6,261,096 B1 | * | 7/2001 | Danger et al. | 433/165 |
| 6,296,485 B1 | * | 10/2001 | Danger | 433/165 |
| 6,715,966 B2 | * | 4/2004 | Tsuzuki et al. | 407/53 |

* cited by examiner

*Primary Examiner*—Todd E. Manahan
(74) *Attorney, Agent, or Firm*—McDonnell Boehnen Hulbert & Berghoff LLP

(57) ABSTRACT

A method and bur is described for preparing a surface of a metal substrate. The bur includes a shank portion and a cutting head. The cutting head includes a base portion connected to the shank portion, a tip portion opposite the base portion and a plurality of similar blades defined by equal size bur grooves formed along a longitudinal axis of the cutting head. Each of the blades including a plurality of spaced dentates defined by a helical groove spiraling from the base portion to the tip portion in a counterclockwise direction about the circumference of the cutting head at an angle departing from a line perpendicular to the longitudinal axis at an angle from about 5 to about 18 degrees.

13 Claims, 2 Drawing Sheets

BUR FOR PREPARING METAL SUBSTRATES

This application claims the benefit of U.S. Provisional Application No. 60/374,094, filed Apr. 19, 2002.

FIELD OF THE INVENTION

The apparatus and method of the present invention generally relates to surface preparation and bonding techniques, such as in the dental field. In particular, the apparatus of the present invention relates to an improved bur and method for the preparation of the surface of an underlying metal structure of a porcelain-fused-to metal restoration, dental crown or the like.

BACKGROUND OF THE INVENTION

The dental laboratory technician is familiar with a variety of methods for preparing a metal substrate prior to porcelain application in the construction of porcelain-to-metal dental crowns and bridges. Generally, the construction of such a porcelain-fused-to-metal or ceramo-metal prosthesis begins with production of a metal casting or substrate. The surface of the metal substrate must be prepared to receive and bond to a porcelain overlay.

The most commonly used materials and method for preparing the metal substrate involves the use of mounted abrasive stones that are attached to a rotary handpiece. When the handpiece is activated the operator uses the rotating abrasive stones to grind the surface of the metal substrate to reduce the thickness of the metal substrate by 0.2 mm to 0.3 mm. The typical handpiece used for this procedure is operated a speed of about 45,000 RPM.

Use of mounted abrasive stones typically requires a great deal of strength in order to apply sufficient pressure to the stones to grind the metal substrate into the desired shape. The amount of pressure and friction created upon the metal substrate can result in significant heat build up at the stone metal interface and may pose a heat hazard to the fingers of the operator. The procedure is typically quite time-consuming as well as somewhat hazardous.

Mounted abrasive stones are constructed of a mixture of various sized stone particles and a cement-like binding substance. The mixture is shaped and mounted upon a mandrel and allowed to harden. It is believed that when a mounted abrasive stone is used to abrade a metal surface, the stone begins to break down. The loosened ingredients in the mounted abrasive stones include particles of abrasive materials mixed with cement and other substances at the stone-metal interface. If these materials are not adequately cleaned from the metal substrate, it can contaminate the porcelain-to-metal interface and compromise the strength of the porcelain-to-metal bond. It is also believed that the metal surface created by abrasive mounted stones may exhibit porosities that cannot be determined by visual inspection. Since the life of the crown is directly related to the bond between the metal substrate and porcelain overlay or veneer, it can be seen that surface preparation and the resulting bond is critical.

A further disadvantage of using abrasive mounted stones involves the change in shape of the stone due to wear over short time, thereby compromising consistency of the finished surface of the metal substrate.

Another tool, which is sometimes used to finish a metal dental substrate, includes a conventional carbide crosscut bur. Although used to a lesser degree than stones, these conventional burs are known to leave in its wake a very smooth surface/finish. It is still believed by some technicians in the art that a smooth satin finish yields a proper surface on which to bond the porcelain. It is believed that these burs leave a smooth or clean surface due to the fact that dentates on adjacent blades or flutes of the bur are oriented to have an amount of overlap that assists in the removal of unwanted material on the entire surface being prepared. However, the conventional crosscut bur has a tendency at a high rotational speed to skip or bounce off the surface to be prepared, which can make it difficult to control and fatiguing to hold and furthermore, necessitates that the bur is used at a relatively low rotational speed, such as about 45,000 RPM.

A demand exists therefore for an improved device and method for preparing metal substrate surfaces for receiving a porcelain veneer. The present invention satisfies the demand.

SUMMARY OF THE INVENTION

In broad overview, the present invention relates to an improved carbide-type bur and a method for finishing metal substrates. As applied in the dental filed, the metal substrate is referred to as a coping (the underlying metal structure of the porcelain fused-to-metal crown) and/or a pontic (the portion of the underlying metal structure of a dental bridge that acts as the replacement for a missing tooth).

The bur and method is used to create a novel textured surface on the metal substrate in preparation for application of porcelain. The resulting surface operates to strengthen the porcelain to metal bond, which creates a strong aesthetically pleasing restoration commonly referred to as a porcelain fused to metal, or ceramo-metal, dental crown or bridge. The invention includes a dental bur specifically designed for use with a high-speed dental handpiece for preparation of the surface. The dental bur is designed to aggressively grind metal with a smooth controllable cutting action when used in a dental handpiece at high speed (i.e., at or about 300,000 RPM). Use of the dental bur results in greater efficiency, increased productivity and less physical stress when preparing metal surfaces for porcelain application.

One aspect of the present invention provides an improved carbide crosscut bur inserted into a dental high-speed handpiece operating at about 300,000 RPM (for example, in a Bienair model). The bur includes a shank portion for insertion into the handpiece and a bur head attached to the shank. The bur head may have a variety of gross shapes including round, oval, ball, sphere, cylindrical, tapered, flat and tapered, cone, flared, inverted cone, round tip and other shapes. Preferably the bur is made of tungsten carbide. The improved bur may include a plurality of blades, for example from about 6 to about 30 or more blades or flutes oriented substantially along the longitudinal axis of the bur. The blades may be formed parallel to the axis of the bur or may be formed offset at an angle with respect to the axis of the bur. Further, the blades may be formed in a helical configuration with respect to the axis of the bur. In a particularly preferred embodiment, the blades are formed in a helical configuration that spiral from left to right extending from the base of the bur head towards the tip of the bur head when viewed in a side view. In other words, the blades may spiral in a helical configuration in a counterclockwise fashion from the base to the tip of the bur.

Each of the blades includes a plurality of dentates or serrations defined by a helical crosscut or groove formed along the length of the bur. The groove is cut at an angle that departs from about 0 to about 20 degrees with respect to a line substantially perpendicular to the bur axis. The groove may be unshaped, v-shaped or rectangular in section or any other suitable shape.

It is a feature of the present invention that the groove defining the dentates of the bur has a specific angular helical rise along the length of the bur. As a result the dentates are formed in a helical fashion about the circumference of the bur head in such a fashion as to be oriented along a line angled from the line perpendicular to the longitudinal axis of the bur counterclockwise from the base toward the tip of the bur. The alignment of dentates on adjacent blades therefore, are aligned along a line which depart at an angle of about 0 to about 20 degrees from a line perpendicular to the longitudinal axis of the bur.

In accordance with a method of the present invention, a dental patient having a porcelain-to-metal crown or bridge made will first schedule an appointment with a dentist who will gather diagnostic information as part of standard treatment. Upon agreement to treatment, the dentist will prepare the patient's affected teeth by reducing the size and shape of the tooth with conventional rotary cutting instruments in preparation for making a dental impression of the teeth. The dentist properly wraps and sends the dental impression to a dental laboratory where the impression will be made into a stone model of the teeth. The laboratory technician pours a mixture of dental die stone into the dental impression. When the die stone is hardened, the dental impression is separated from the hardened die stone to reveal a stone model of the prepared teeth and those adjacent to it. The stone dental model is used to replicate the patient's dentition, and displays the teeth that the dentist prepared for construction of a porcelain-fused-to-metal crown or bridge.

The laboratory technician prepares the stone dental model in accordance with standard procedures for pinning and indexing the stone dies of the teeth for which a porcelain-fused-to-metal restoration is to be made. The individual pin-indexed dies of the prepared teeth are separated from the stone model, trimmed at the prepared margin, and a die hardener applied. Wax is then placed on the prepared surface of the stone die to cover the stone die and form a wax substrate with a collar at the marginal area. This substrate will be sprued and placed in an investment material. The investment is then heated to such a degree as to melt and dissolve the wax and molten metal alloy is allowed to fill the prepared cavity in the investment. The hot metal flows into the investment replicating the design of the wax pattern that is dissolved in the process.

When the newly formed metal substrate has been allowed to cool, the metal substrate is removed from the casting sprue, at which point the surface of the metal substrate must be prepared, i.e., given a textured finish according to the present invention, before the porcelain mixture is applied. The metal substrate is prepared using the bur of the present invention, i.e., the improved bur in a lateral motion over the surface of the metal substrate to cut the metal surface in a uniform manner.

The technician will utilize a high-speed dental handpiece (e.g., a Bienair model) operating at a speed of about 300,000 rpm with the improved bur, or burs, and may choose an assortment of shapes as required for the task at hand. The technician will reduce the bulk of metal substrate that has been left by the casting sprue. During this bulk reduction the technician will measure the thickness of the metal substrate using a caliper gauge and proceed to finish the metal substrate to an overall thickness of about 0.5 mm. While using the high-speed dental hand piece and inventive bur, the technician is able to reduce the metal substrate with physical ease and control, and with efficient speed (compared to traditional methods with abrasive stones) thereby greatly reducing the working time needed for each metal substrate.

It is also the intent of this method used with the specialized bur to render a more bondable surface with a scored or corrugated texture that will promote an increased mechanical, chemical and compressive bond strength of the porcelain to the metal substrate surface. In use of the inventive bur, the technician cuts the surface of the metal surface (as opposed to grinding the metal surface) thereby leaving the surface free of debris and clean of any contaminants which can become impregnated in the metal surface and reduce the bond strength of porcelain to metal by moving the bur in a lateral motion across the metal substrate surface.

In cases where a dental technician is constructing a dental bridge to replace missing teeth, the technician fabricates one or more replacements (pontics) to bridge the gap between existing teeth (abutment teeth). If a pontic(s) is involved (a solid support for a missing tooth) the technician reduces the metal surface(s) of the pontic in such a way as to resemble the adjacent coping, using the described method and specialized bur(s) where needed. When the reduction of metal is complete and the metal substrate is gauged at about 0.3 mm to 0.5 mm at its thinnest point, the technician readies the metal surface for application of porcelain.

At this point the metal substrate may be air abraded with aluminous oxide delivered under air pressure. The metal substrate may then be placed in an ultrasonic bath for cleaning after which it is placed on a tray and put inside a porcelain oven, which is brought to a suitable temperature for proper oxidation and degassing as is known in the art.

Now the surface is properly conditioned for opaque porcelain application. When the opaque layer is applied and fired, the interface of the metal and porcelain at the surface of the metal substrate is said to have a greater bond strength, because of its mechanical, chemical and compressive bonding attributes. An unexpected benefit of the corrugated surface of the metal substrate underlying the porcelain material is a more life-like coloration of the restoration, which is believed to diffuse light in a manner more closely like that of the natural tooth material.

Once the surface of the metal substrate is opaqued, it is now prepared to receive additional porcelain mixtures, applied in a series of applications, shaped into the form and design of a tooth, and fired in a porcelain oven. Upon completion of the porcelain being fired, it is cooled, glazed and finished, the edges and inside surface of the metal substrate are polished, and the finished dental restoration is sent to the prescribing dentist for cementation or bonding to the patient's tooth.

One aspect of the present invention provides a dental bur for preparing a surface of a metal substrate including a shank portion and a cutting head. The cutting head includes a base portion connected to the shank portion, a tip portion opposite the base portion and a plurality of similar blades defined by equal size bur grooves formed along a longitudinal axis of the cutting head. Each of the blades including a plurality of spaced dentates defined by a helical groove spiraling from the base portion to the tip portion in a counterclockwise direction about the circumference of the cutting head at an angle departing from a line perpendicular to the longitudinal axis at an angle from about 0 to about 20 degrees.

Other aspects of the invention provide a helical groove section with a u-shape, v-shape, rectangular, oval, elliptical, wave-shaped, or ogee-shape. The dentates may be generally triangular in section or rectangular in section. The dentates may include a forward cutting surface. The bur may include six to thirty or more blades. Each blade may include from 4 to 30 or more dentates formed therealong. An overall sectional shape of the cutting head may be one of round, oval, bud, cylindrical, conical, frusto-conical and tapered. The tip of the cutting head may be rounded or flat, for example. Each of the plurality of blades may be aligned with the longitudinal axis, offset at an angle with respect to the longitudinal axis or helically oriented with respect to the longitudinal axis. The plurality of blades may be oriented parallel to the longitudinal axis, helically oriented in a counterclockwise direction extending from the base portion to the tip portion with respect to the longitudinal axis. The cutting head, when contacted in a lateral motion across a surface of a metal substrate, forms a plurality of parallel grooves in the surface. The cutting head, when contacted in a lateral motion across a metal substrate, may form a corrugated surface. The cutting head, when contacted in a lateral motion across a surface of a metal substrate, forms a plurality of parallel grooves in the surface. The plurality of parallel grooves may be saw tooth in section. The plurality of parallel grooves may be rectangular in section. The plurality of parallel grooves may be sinusoid in section. The plurality of parallel grooves may be ramp-shaped in section. The plurality of dentates may include dentates that differ from others in the same bur with respect to shape and size.

Another aspect of a method of the present invention provides a method of forming a textured porcelain-receiving surface in a metal substrate including providing a dental bur for preparing the surface. The dental bur including a shank portion and a cutting head including a base portion connected to the shank portion. A tip portion is positioned opposite the base portion and a plurality of similar blades defined by equal size grooves are formed along a longitudinal axis of the cutting head. Each of the blades includes a plurality of spaced dentates defined by a helical groove spiraling from the base portion to the tip portion in a counterclockwise direction about the circumference of the cutting head at an angle departing from a line perpendicular to the longitudinal axis at an angle from about 0 to about 20 degrees. The metal substrate is contoured with the dental bur to a desired thickness and contour. Forming a plurality of parallel grooves in the porcelain-receiving surface finishes the porcelain-receiving surface.

Another aspect of a method of the present invention provides a method of forming a porcelain-fused-to-metal construct includes providing a metal substrate. A dental bur is provided for finishing a porcelain-receiving surface of the metal substrate. The dental bur includes a shank portion and a cutting head with a base portion connected to the shank portion. A tip portion is formed opposite the base portion and a plurality of similar blades defined by equal size grooves formed along a longitudinal axis of the cutting head. Each of the blades include a plurality of spaced dentates defined by a helical groove spiraling from the base portion to the tip portion in a counterclockwise direction about the circumference of the cutting head at an angle departing from a line perpendicular to the longitudinal axis at an angle from about 0 to about 20 degrees. The metal substrate is contoured with the dental bur to a desired thickness and contour. Forming a plurality of parallel grooves in the porcelain-receiving surface finishes the porcelain-receiving surface and a porcelain material is applied to the porcelain-receiving surface.

The invention provides the foregoing and other features, and the advantages of the invention will become further apparent from the following detailed description of the presently preferred embodiment, read in conjunction with the accompanying drawings. The detailed description and drawings are merely illustrative of the invention and do not limit the scope of the invention, which is defined by the appended claims and equivalents thereof. In that regard, while discussed primarily with respect to a dental application, both the bur and the inventive method could have application outside of that field.

DETAILED DESCRIPTION OF A PRESENTLY PREFERRED EMBODIMENT

Figure 1:
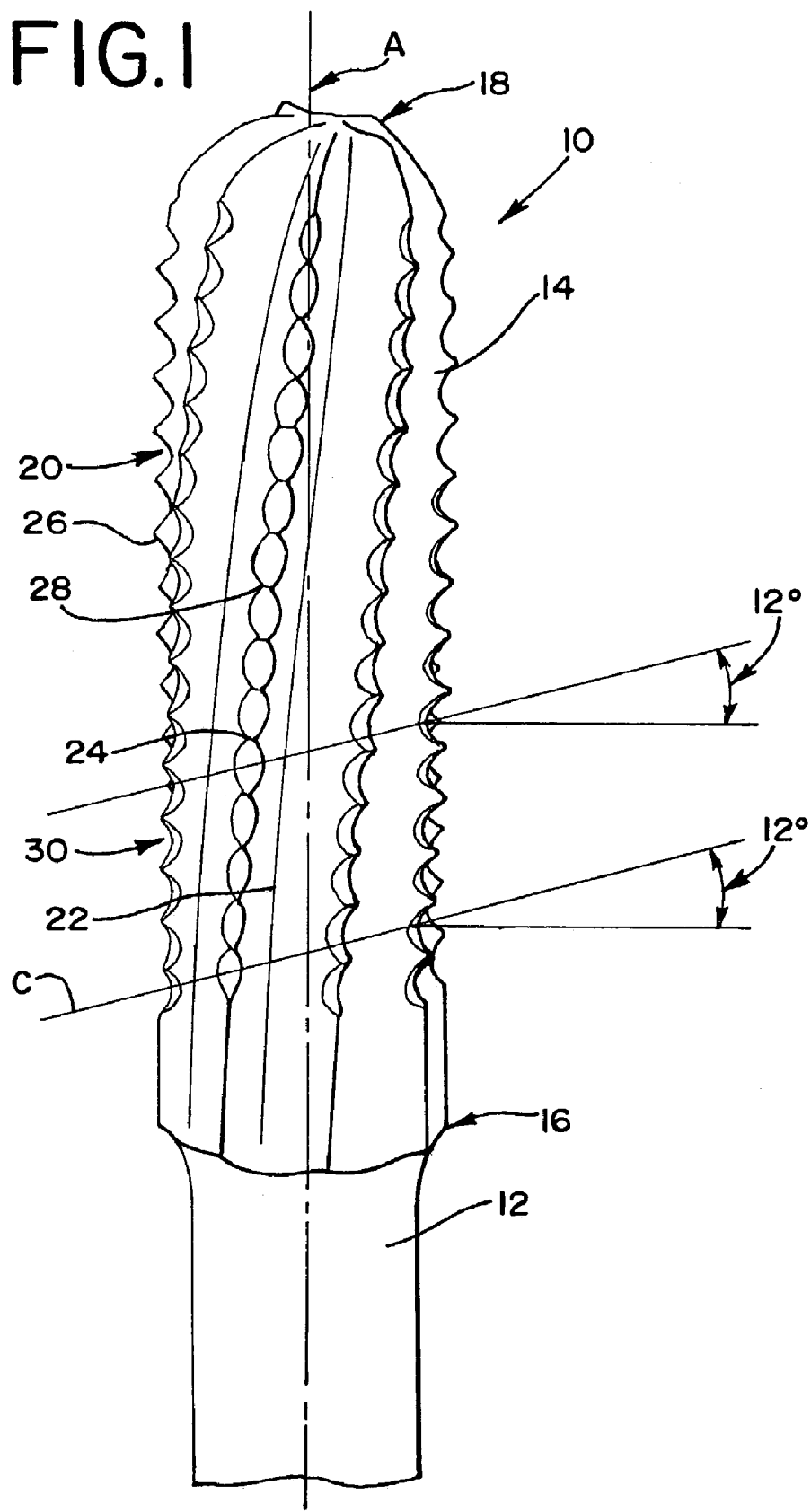
FIG. 1 is a side view of an embodiment of the bur according to the present invention.

FIG. 1 shows a fluted or bladed carbide bur 10 of the present invention. The bur 10 may be of a unitary construction, i.e., made of a single piece of tungsten carbide or the like. In the alternate, the bur may be made of separate elements; all made of tungsten carbide or any similar suitable material or made of different materials suitably connected. The bur 10 shown generally comprises a shank portion 12. The shank 12 may be made of any suitable material, such as stainless steel. At a distal or free end of the bur 10 a cutting head 14 is formed, which is commonly referred to as a bur head. The cutting head 14 is preferably comprised of a carbide material, for example, tungsten carbide or a material with similar properties, which may be formed into a cutting configuration. Other suitable cutting head materials include diamond and ceramic materials.

The cutting head 14 and shank 12 are coaxially aligned with a longitudinal axis A. The cutting head 14 extends outwardly from the shank 12 and may be a cylindrical, round, ball, cone, elliptical, or like overall shape. In one embodiment, the cutting head 14 has a frusto-conical shape that tapers in diameter from a base portion 16 toward a tip portion 18 of the cutting head 14. The cutting head may have a length measured along the longitudinal axis of about 3 to 10 mm or longer in length.

The cutting head 14 includes an outer surface 20 having similar cutting members 22 extending outwardly from the outer surface. It is understood that diamonds or other durable cutting materials may selectively be employed as the material of the cutting members 22 at the outer surface of the cutting head.

Each cutting member 22 may be referred to as a blade or flute, one of which is shown at 24. Each cutting member 22 extends along the length (longitudinally) of the cutting head 14. Each blade 24 may be straight and aligned parallel to the longitudinal axis A of the bur 10. In an alternate embodiment, each blade 24 may be angled away from the longitudinal axis A. In a preferred embodiment, each blade 24 may be arranged in a helical, arcuate or spiral fashion counterclockwise about the periphery of the cutting head 14. Each blade 24 is generally parallel to the longitudinal axis A of the cutting head 12 at a helix angle of preferably two degrees. However, an acceptable range for the helix angle of each blade 24 is zero degrees (0°) to 30 degrees (30°).

Each blade 24 includes a periphery of cutting teeth referred to as dentates 26 formed along the length of each blade 24. Each blade 24 may include any suitable number of dentates 26, for example from 5 to 40 tooth shaped dentates. Each dentate 26 is formed with a forward cutting surface 28. The dentates 26 and the cutting surface thereof 28 may be triangular, rectangular or any suitable cutting shape. The dentates 26 are formed in the cutting members 22 by a counterclockwise crossing cut 30, as described along line C, as oriented from the base portion 16 to the tip portion 18 across a right section of the cutting head 14 at a constant oblique angle. The angle of the crossing cut 30 may be from about 0 to 20 degrees. The crossing cut 30 or helical cross groove may be u-shaped as shown or v-shaped, rectangular or ogee shaped, for example.

Figure 2:
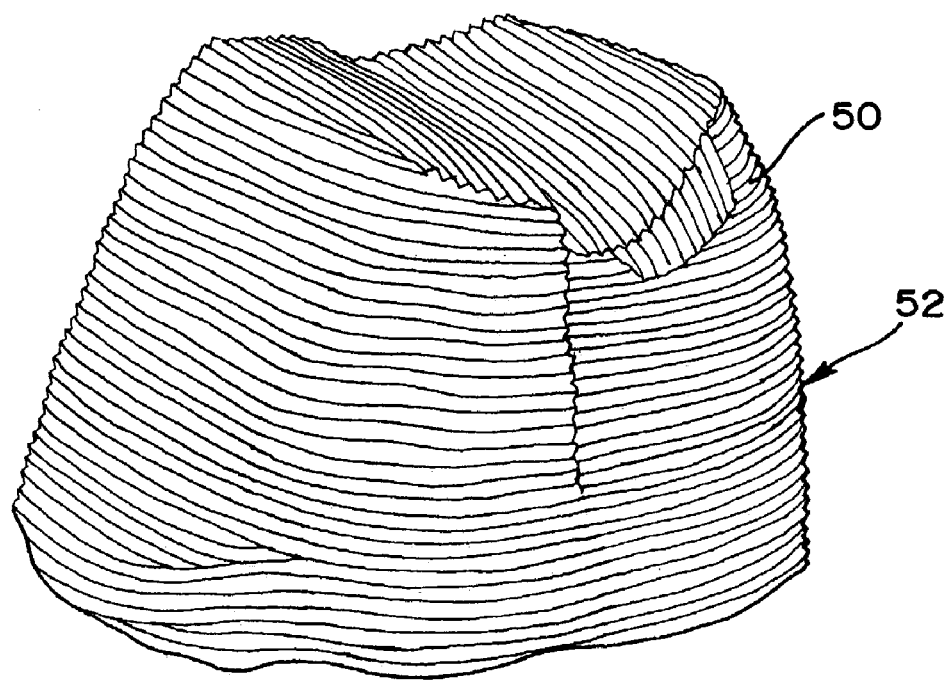
FIG. 2 is a perspective view of one embodiment of a surface on a metal substrate prepared by the bur of FIG. 1 by the method of the present invention.
Figure 3:
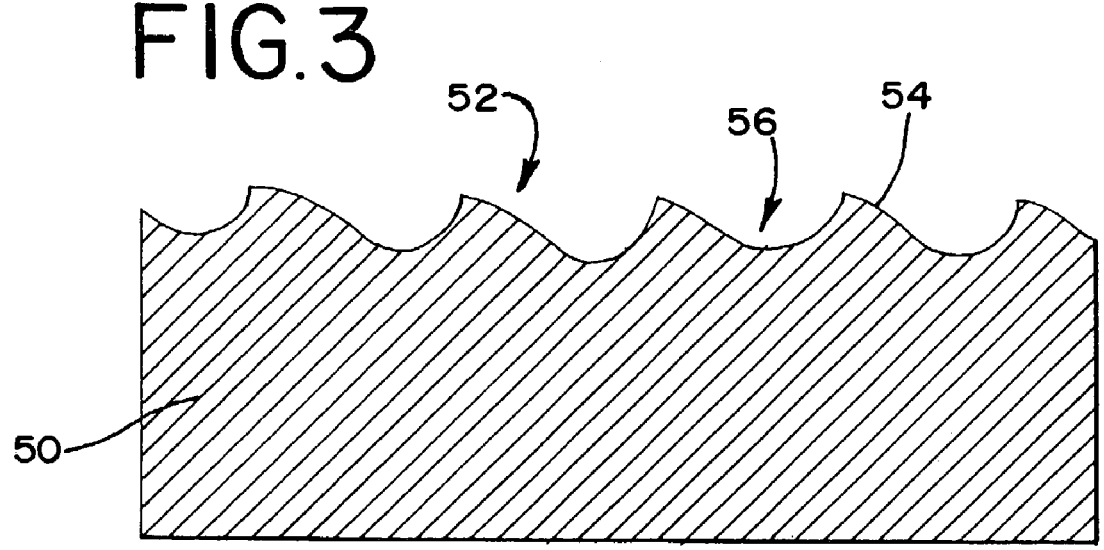
FIG. 3 is a cross-sectional view of an embodiment of a surface prepared by the bur and method of the present invention.

FIG. 2 shows a metal substrate 50 prepared by the bur and method of the present invention. The metal substrate includes a corrugated surface 52, which has a longitudinal grooved appearance when viewed in perspective or a wave appearance in cross section (perpendicular to a longitudinal axis of the grooves, see FIG. 3). In other words, the surface 52 includes convex tooth-like raised portions 54 alternating with concave grooves 56.

It will be understood that the overall envelope or shape of the surface 52 will be determined in part by the shape of the bur dentates 26 and crossing cuts therebetween. For example, if the dentates 26 are rectangular, the grooves 56 will tend to have a flat bottom and so on. Further, the angle along line C will contribute to determine cut geometry in that, if successive dentates 25 are aligned by the angle of line C and a direction of lateral manipulation by a technician, then the pattern of raised portions 54 and grooves 56 will closely match that of the inverse of the pattern of dentates 26 and cut 30. In other words, a square dentate 26 will create a square groove 56 in the surface 52 and an arcuate cut 30 will produce a rounded or arcuate raised portion 54. If the angle along line C causes successive dentates 26 to be misaligned to some degree, the grooves 6 may be wider in section that the raised portions 54. It will be appreciated that a large variation in corrugated surfaces 52 may be produced by subtle changes in bur configuration and that the object, at least in part, is to produce a grooved or corrugated surface with an increased surface area compared to a conventional smooth satin surface as in the prior art. In this manner, a porcelain-fused-to metal bond with greatly enhanced strength may be produced in less time and effort than previously known and with less risk of contamination.

It should be appreciated that the embodiments described above are to be considered in all respects only illustrative and not restrictive. The scope of the invention is indicated by the following claims rather than by the foregoing description. All changes that come within the meaning and range of equivalents are to be embraced within their scope.

What is claimed is:

1. A bur for preparing a surface of a metal substrate comprising:
    a shank portion; and
    a cutting head including a base portion connected to the shank portion, a tip portion opposite the base portion and a plurality of similar blades defined by equal size bur grooves extending between the cutting head base portion and the tip portion, each of said blades including a plurality of continuous dentates defined by a helical groove spiraling from the base portion to the tip portion in a counterclockwise direction about the circumference of said cutting head at an angle departing from a line perpendicular to a longitudinal axis at an angle greater than 0 to about 10 degrees.

2. The bur of claim 1 wherein said dentates are triangular in cross section.

3. The bur of claim 1 wherein said dentates include a forward cutting surface.

4. The bur of claim 1 wherein said plurality of blades include six blades.

5. The bur of claim 1 wherein said plurality of blades include eight blades.

6. The bur of claim 1 wherein said plurality of blades number from about six to about 60 blades.

7. The bur of claim 1 wherein each of said plurality of blades include from about 4 to about 100 dentates formed therealong.

8. The bur of claim 1 wherein each of said plurality of blades include from about 8 to about 38 dentates formed therealong.

9. The bur of claim 1 wherein an overall longitudinal sectional shape of said cutting head is cylindrical.

10. The bur of claim 9 wherein the tip of said cutting head is rounded.

11. The bur of claim 1 wherein each of said plurality of blades is offset at an angle with respect to said longitudinal axis.

12. The bur of claim 1 wherein said dentates are arranged on said cutting head so as to form a plurality of parallel grooves in a metal material, when said material is contacted in a lateral motion by said cutting head.

13. The bur of claim 1 wherein said dentates are arranged on said cutting head so as to form, a corrugated surface in a material when said material is contacted in a lateral motion by said cutting head.

* * * * *